US012144528B2

(12) United States Patent
Sommers et al.

(10) Patent No.: US 12,144,528 B2
(45) Date of Patent: Nov. 19, 2024

(54) BONE FIXATION SYSTEMS AND NAIL HAVING COMPRESSIVE THREADING

(71) Applicant: Acumed LLC, Hillsboro, OR (US)

(72) Inventors: Mark B. Sommers, Beaverton, OR (US); Steven P. Horst, Dayton, OR (US); James G. Falkner, Jr., Beaverton, OR (US); Scott F. Mastroianni, Forest Grove, OR (US); Bill McNabb, Hillsboro, OR (US); Gregory D. Hutton, Aloha, OR (US)

(73) Assignee: Acumed LLC, Hillsboro, OR (US)

(*) Notice: Subject to any disclaimer, the term of this patent is extended or adjusted under 35 U.S.C. 154(b) by 0 days.

(21) Appl. No.: 17/825,618

(22) Filed: May 26, 2022

(65) Prior Publication Data

US 2022/0378484 A1 Dec. 1, 2022

Related U.S. Application Data

(60) Provisional application No. 63/194,456, filed on May 28, 2021.

(51) Int. Cl.
*A61B 17/72* (2006.01)
*A61B 17/86* (2006.01)

(52) U.S. Cl.
CPC ........ *A61B 17/7233* (2013.01); *A61B 17/863* (2013.01); *A61B 17/8645* (2013.01)

(58) Field of Classification Search
CPC .............. A61B 17/7233; A61B 17/863; A61B 17/8645

(Continued)

(56) References Cited

U.S. PATENT DOCUMENTS 5,352,228 A * 10/1994 Kummer ............ A61B 17/1725
606/98
5,549,609 A 8/1996 Frankel et al.
(Continued)

FOREIGN PATENT DOCUMENTS

CN 209884292 U 1/2020
WO 2017125476 A1 7/2017

OTHER PUBLICATIONS

International Search Report corresponding to related International Patent Application No. PCT/US2022/031140 mailed Sep. 13, 2022, 3 pages.

(Continued)

*Primary Examiner* — Eduardo C Robert
*Assistant Examiner* — David C Comstock
(74) *Attorney, Agent, or Firm* — K&L Gates LLP

(57) ABSTRACT

A nail for compressing two bone parts to treat bone fractures or osteotomies is provided. The nail has an elongate smooth portion and an elongate threaded portion that is constructed for generating axial compression along a length of the elongate threaded portion between two bone parts. The nail may also have one or more apertures for installing one or more crossing screws through the nail. An installation instrument particularly constructed to install the provided nail is provided. A first and second portion of the provided nail installation instrument may rotate relative to one another when a locking mechanism is disengaged, but are locked in position relative to one another when the locking mechanism is engaged, which enables installation of the provided nail.

18 Claims, 7 Drawing Sheets

(58) Field of Classification Search
USPC .................................................. 606/62, 64
See application file for complete search history.

(56) References Cited

U.S. PATENT DOCUMENTS

| | | | |
|---|---|---|---|
| 5,665,087 A | 9/1997 | Huebner | |
| 6,517,541 B1 | 2/2003 | Sesic | |
| 7,144,399 B2* | 12/2006 | Hayes | A61B 17/1725 |
| | | | 606/98 |
| 9,192,398 B2* | 11/2015 | Siravo | A61B 17/1725 |
| 9,241,744 B2* | 1/2016 | Blake | A61B 17/7225 |
| 10,499,960 B2* | 12/2019 | Sinnott | A61B 17/8872 |
| 2003/0074000 A1* | 4/2003 | Roth | A61B 17/744 |
| | | | 606/62 |
| 2004/0210227 A1* | 10/2004 | Trail | A61B 17/8635 |
| | | | 606/328 |
| 2005/0096656 A1* | 5/2005 | Behrens | A61B 17/1725 |
| | | | 606/64 |
| 2009/0062797 A1* | 3/2009 | Huebner | A61B 17/1739 |
| | | | 606/151 |
| 2009/0093813 A1* | 4/2009 | Elghazaly | A61B 17/1725 |
| | | | 606/62 |
| 2013/0274818 A1 | 10/2013 | Goshayeshgar et al. | |
| 2014/0188113 A1* | 7/2014 | Overes | A61B 17/1739 |
| | | | 606/64 |
| 2016/0310176 A1 | 10/2016 | Van Dyke et al. | |
| 2019/0125418 A1* | 5/2019 | Muller | A61B 17/1604 |
| 2020/0405329 A1* | 12/2020 | Liu | A61B 17/8645 |

OTHER PUBLICATIONS

International Written Opinion corresponding to related International Patent Application No. PCT/US2022/031140 mailed Sep. 13, 2022, 6 pages.

International Preliminary Report corresponding to related International Patent Application No. PCT/US2022/031140 mailed Dec. 7, 2023, 8 pages.

* cited by examiner

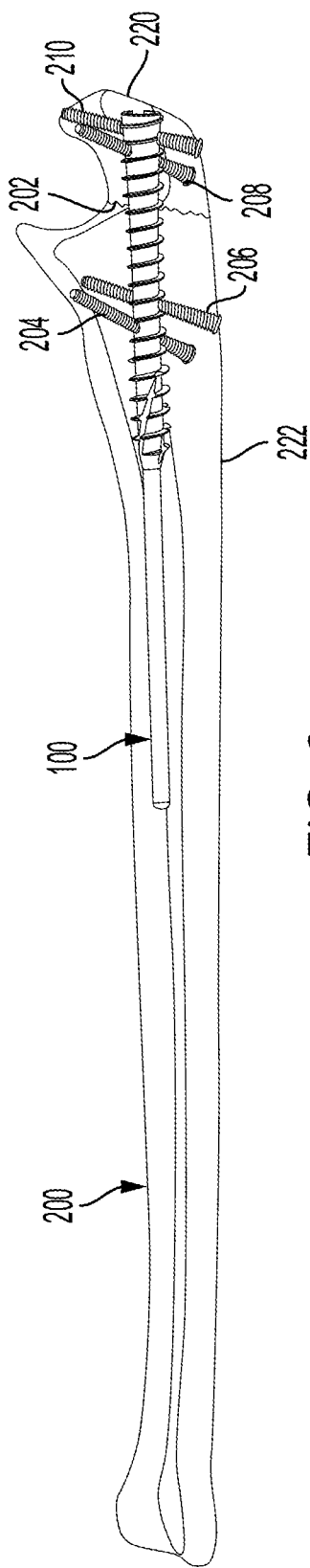
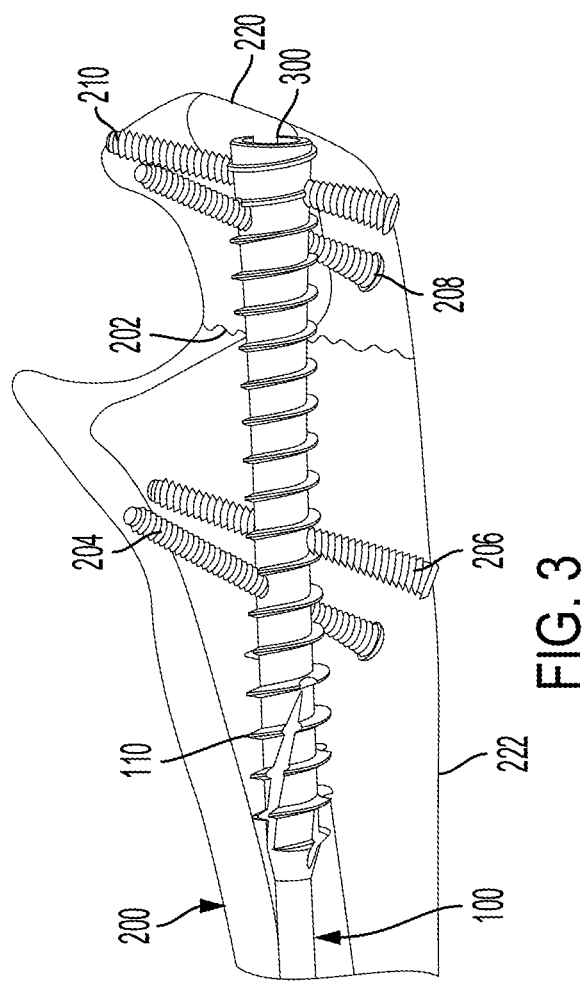
FIG. 2
FIG. 3

BONE FIXATION SYSTEMS AND NAIL HAVING COMPRESSIVE THREADING

PRIORITY CLAIM

This application claims priority to U.S. Provisional Patent Application No. 63/194,456 filed on May 28, 2021, the entire contents of which are hereby incorporated by reference and relied upon.

BACKGROUND

Treating certain fractures or osteotomies, such as olecranon fractures or osteotomies, can typically be hardware intensive involving plating, pins, wires, and/or other fixation implants. For instance, muscle tension of the triceps constantly applies force to the proximal ulna thereby requiring strong fixation when treating an olecranon fracture or osteotomy to counteract force from the triceps. One of the challenges of fixing the olecranon is that the fragment is fairly small and there is not much bone for screw fixation to effect strong fixation. In certain cases, fixation implants used for treating fractures or osteotomies can have an undesired prominence from the bone thereby causing undesired pain or irritation to a patient. In other cases, such fixation implants can have less than desired fixation strength which may sometimes result in losing reduction.

One typical technique for treating olecranon fractures or osteotomies is by using pins and cerclage wire. In this technique, a surgeon inserts typically two or more pins with eyelets, or bend over pins, through the olecranon fragment into the bone. The surgeon then loops a cerclage wire through the inserted pins and through a hole formed through the ulna shaft, and tensions the looped cerclage wire by creating a twisted knot. The pins and cerclage wire are typically left in place after the olecranon heals. The main advantage of the pins and cerclage wire technique is that it is a low cost option. The holding power of the pins and cerclage wire technique, however, is limited because the cerclage wire construct stretches over time, which can thereby cause reduction loss. Further, the pins and the cerclage wire (particularly the twisted knot of the cerclage wire) are prominent from the bone and can cause soft tissue irritation. For instance, a patient does not have much soft tissue coverage near the patient's elbow and can therefore feel the pins and cerclage wire under the patient's skin, which can be painful and irritating.

Another typical technique for treating olecranon fractures or osteotomies is with a typical intramedullary nail and crossing screws. As stated above, however, the olecranon fragment is fairly small and there is not much bone for screw fixation to effect strong fixation. As such, a typical intramedullary nail and crossing screws may not provide sufficient holding power in some cases to allow the olecranon fracture or osteotomy to heal properly.

A further typical technique for treating olecranon fractures or osteotomies is the plating technique. In the plating technique, a surgeon fixes a pre-contoured plate to the ulna shaft that grabs the proximal olecranon fragment and pulls it towards the main portion of the ulna shaft. The advantage of the plating technique is that it is a stable construct with a high degree of fixation strength. The pre-contoured plate construct, however, is much more expensive than the pins and cerclage wire technique. Additionally, a large incision is required to install the plate and screws which can be undesirable for patient. Further, the plate and screws are prominent from the bone, even more so than the pins and cerclage wire, and can therefore cause significant pain or irritation for the patient. The plate and screws must also be removed after the olecranon heals, which requires a second surgery.

Accordingly, a need exists for a technique for treating an olecranon fracture or osteotomy involving instrumentation with a desired fixation strength and a reduced prominence from the bone as compared to typical techniques.

SUMMARY

The present disclosure provides new and innovative systems and nails for securing and compressing bone parts separated by a fracture. In certain aspects, the provided systems and nails may be particularly suited for olecranon fracture stabilization. An example system for compressing a first bone part and a second bone part separated by a fracture includes a nail having an elongate smooth portion and an elongate threaded portion, the elongate smooth portion including a leading end of the nail and the elongate threaded portion including a trailing end of the nail, the elongate threaded portion including a first end opposite the trailing end and a thread extending from the first end to the trailing end, wherein the thread has a decreasing pitch from the first end to the trailing end, and wherein the elongate threaded portion further includes at least one aperture extending through a central axis of the nail; and at least one screw sized to be positioned through the at least one aperture.

In an aspect of the present disclosure, which may be combined with any other aspect listed herein unless specified otherwise, the at least one aperture comprises a first aperture and a second aperture each extending through the central axis of the nail.

In an aspect of the present disclosure, which may be combined with any other aspect listed herein unless specified otherwise, a central axis of the first aperture is at an angle to a central axis of the second aperture.

In an aspect of the present disclosure, which may be combined with any other aspect listed herein unless specified otherwise, the at least one aperture further comprises a third aperture and a fourth aperture each extending through the central axis of the nail.

In an aspect of the present disclosure, which may be combined with any other aspect listed herein unless specified otherwise, a central axis of the third aperture is at an angle to a central axis of the fourth aperture.

In an aspect of the present disclosure, which may be combined with any other aspect listed herein unless specified otherwise, the first, second, third, and fourth apertures are positioned along the elongate threaded portion such that, when the elongate threaded portion of the nail is installed across the fracture separating the first bone part and the second bone part, the first and second apertures are within the first bone part and the third and fourth apertures are within the second bone part.

In an aspect of the present disclosure, which may be combined with any other aspect listed herein unless specified otherwise, the system further comprises a nail installation instrument having a first portion configured to couple to the trailing end of the nail, wherein the first portion of the nail installation instrument is configured to rotate with the coupled nail independently from a second portion of the nail installation instrument.

In an aspect of the present disclosure, which may be combined with any other aspect listed herein unless specified otherwise, the second portion of the nail installation instrument includes a targeting connector coupled to a targeting block and to the first portion of the nail installation instrument, the targeting block including a plurality of guide holes each configured to receive a cannula.

In an aspect of the present disclosure, which may be combined with any other aspect listed herein unless specified otherwise, the targeting connector is configured to translate a key into or out of a slot of the first portion of the nail installation instrument so as to respectively prevent or enable rotation of the first portion of the nail installation instrument relative to the second portion of the nail installation instrument.

In an aspect of the present disclosure, which may be combined with any other aspect listed herein unless specified otherwise, the first bone part is a first olecranon fragment and the second bone part includes a distal ulna.

In some examples, a method for compressing a first bone part and a second bone part separated by a fracture is provided. The method includes forming a hole in the first bone part, across the fracture, and in the second bone part; coupling a nail installation instrument to a nail, the nail having an aperture extending through a central axis of the nail; inserting part of the nail into the formed hole; rotating a first portion of the nail installation instrument independent of a second portion of the nail installation instrument thereby installing the nail in the formed hole; rotating the second portion of the nail installation instrument independent of the first portion of the nail installation instrument thereby aligning the second portion of the nail installation instrument with respect to the aperture of the installed nail; and installing a screw into the first bone part or the second bone part and through the aperture of the installed nail.

In an aspect of the present disclosure, which may be combined with any other aspect listed herein unless specified otherwise, the nail installation instrument is coupled to the nail prior to inserting part of the nail into the formed hole.

In an aspect of the present disclosure, which may be combined with any other aspect listed herein unless specified otherwise, the method further includes locking the second portion of the nail installation instrument relative to the first portion of the nail installation instrument upon the second portion of the nail installation instrument being aligned with respect to the aperture of the installed nail.

In an aspect of the present disclosure, which may be combined with any other aspect listed herein unless specified otherwise, the second portion of the nail installation instrument includes a targeting block having a plurality of guide holes, the method further comprising inserting a cannula through a guide hole of the targeting block such that the cannula is aligned with the aperture of the installed nail.

In an aspect of the present disclosure, which may be combined with any other aspect listed herein unless specified otherwise, the hole is a first hole, the method further comprises inserting a drill through the cannula and forming, via the drill, a second hole in the first bone part or the second bone part and through the aperture of the installed nail.

In an aspect of the present disclosure, which may be combined with any other aspect listed herein unless specified otherwise, the nail has an elongate smooth portion and an elongate threaded portion, the elongate smooth portion including a leading end of the nail and the elongate threaded portion including a trailing end of the nail, the elongate threaded portion including a first end opposite the trailing end and a thread extending from the first end to the trailing end, wherein the thread has a decreasing pitch from the first end to the trailing end.

In an aspect of the present disclosure, which may be combined with any other aspect listed herein unless specified otherwise, the nail is installed in the formed hole such that the elongate threaded portion is positioned in both the first bone part and the second bone part and across the fracture.

In an aspect of the present disclosure, which may be combined with any other aspect listed herein unless specified otherwise, installing the nail in the formed hole thereby compresses the first bone part and the second bone part against one another at the fracture.

In an aspect of the present disclosure, which may be combined with any other aspect listed herein unless specified otherwise, the part of the nail that is inserted into the formed hole is the elongate smooth portion of the nail, wherein the elongate smooth portion of the nail is inserted into the formed hole prior to rotating the first portion of the nail installation instrument independent of the second portion of the nail installation instrument.

In an aspect of the present disclosure, which may be combined with any other aspect listed herein unless specified otherwise, the first bone part is a first olecranon fragment and the second bone part includes a distal ulna.

Additional features and advantages of the disclosed method and apparatus are described in, and will be apparent from, the following Detailed Description and the Figures. The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the inventive subject matter.

BRIEF DESCRIPTION OF THE DRAWINGS

FIG. 2 illustrates the nail of FIG. 1 installed within an ulna, according to an aspect of the present disclosure.

FIG. 3 illustrates a magnified view of FIG. 2 showing the nail of FIG. 1 installed across an olecranon fracture, according to an aspect of the present disclosure.

DETAILED DESCRIPTION

Figure 1:
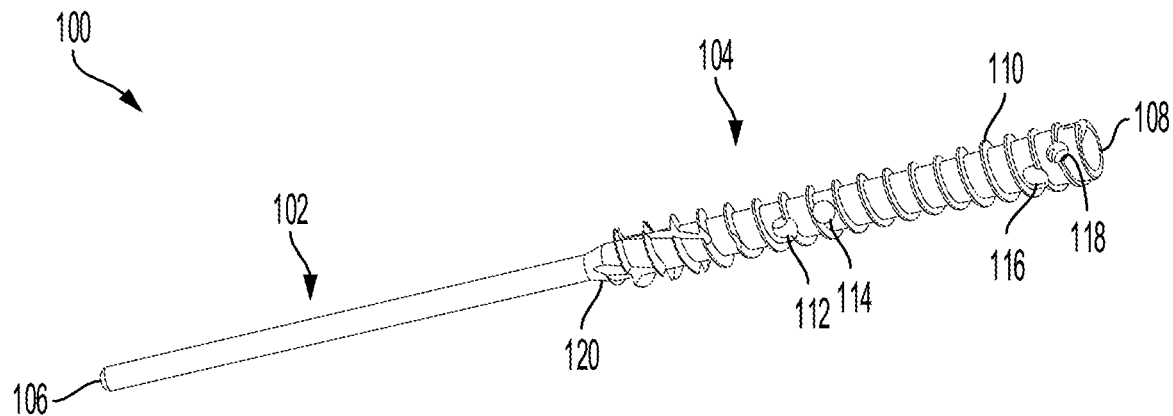
FIG. 1 illustrates a perspective view of a nail, according to an aspect of the present disclosure.

The present application provides new and innovative systems and methods for compressing two bone parts to treat bone fractures or osteotomies. A nail is provided having an elongate smooth portion and an elongate threaded portion that is constructed for generating axial compression along a length of the elongate threaded portion between two bone parts when the nail is installed such that the threaded portion is across a fracture between the two bone parts. For instance, a thread of the elongate threaded portion may have a decreasing pitch moving towards the trailing end of the nail. The nail may also have one or more apertures for installing one or more crossing screws through the nail. The one or more crossing screws can help increase holding power and provide additional stability in both the axial and rotational directions. In some examples, the provided nail can have two apertures that are at an angle to one another such that diverging crossing screws may be installed. In some examples, the provided nail can have two sets of two apertures that are at an angle to one another, one set on either side of the fracture, so that divergent crossing screws may be installed on either side of the fracture.

The combination of the compression afforded by the elongate threaded portion of the presently disclosed nail and the holding power and stability afforded by the one or more crossing screws through the nail provides superior fracture stabilization as compared to both the typical pin and cerclage wire technique and the typical intramedullary nail technique. Additionally, the provided nail and one or more crossing screws have minimal to no prominence from the bone when installed, which thereby reduces pain and irritation to the patient as compared to both the typical pin and cerclage wire technique and the plating technique. While the provided nail may be particularly beneficial for treating olecranon fractures or osteotomies, the provided nail may also be used to effect compression for treating fractures or osteotomies of other suitable bones.

A nail installation instrument is further provided that is particularly constructed to install the provided nail, which involves rotating the nail because of the nail's threaded portion. A typical nail installation instrument is rigidly coupled to a typical intramedullary nail during installation without relative movement between the nail and the guide in order to maintain alignment between the instrument's targeting guide and the nail so that one or more crossing screws may be installed through the nail using the targeting guide. A typical intramedullary nail, however, is smooth along its length and is therefore not rotated during installation. Conversely, the provided nail is rotated during installation and therefore a typical nail installation instrument constructed for rigid coupling cannot be used to install the provided nail.

In contrast to typical nail installation instruments, the provided nail installation instrument allows selectively free rotation between two different portions of the provided nail installation instrument. Stated differently, a first and second portion of the provided nail installation instrument may rotate relative to one another when a locking mechanism is disengaged, but are locked in position relative to one another when the locking mechanism is engaged. The first portion of the nail installation instrument may couple to a trailing end of the provided nail. With the locking mechanism disengaged, the first portion of the nail installation instrument may rotate with a coupled nail independently from the second portion of the nail installation instrument, thereby enabling installation of the provided nail.

The second portion of the nail installation instrument may include a targeting block and a targeting connector that couples the targeting block to the first portion of the nail installation instrument. The targeting connector may be constructed to include the locking mechanism. Because the provided nail is rotated during installation, a position of the targeting block must be adjusted so that it is aligned relative to the one or more apertures of the nail to allow crossing screw installation. To do so, with the locking mechanism disengaged, the second portion of the nail installation instrument may be rotated independently from the first portion of the nail installation instrument until the locking mechanism engages. The provided nail and nail installation instrument are constructed such that the one or more apertures of the nail are aligned with the targeting block when the locking mechanism is engaged. With the first and second portions of the nail installation instrument locked relative to one another, one or more crossing screws may be installed in a typical manner.

FIG. 1 illustrates a perspective view of an example nail 100. The example nail 100 includes a body having an elongate smooth portion 102 adjacent and elongate threaded portion 104. The elongate smooth portion 102 includes a leading end 106 of the nail 100. The elongate threaded portion 104 includes a thread 110 and extends between a trailing end 108 of the nail 100 and an intermediate end 120 at which the elongate threaded portion 104 meets the elongate smooth portion 102. The thread 110 may be constructed so as to generate axial compression, between two bone parts, along a length of the elongate threaded portion 104 when the elongate threaded portion 104 is installed across a fracture between the two bone parts. For instance, the thread 110 may have a variable pitch such that the pitch of the thread 110 continuously decreases from the intermediate end 120 to the trailing end 108. In some aspects, the trailing end 108 of the nail 100 may include a notch 300 (FIG. 3).

In various aspects, the elongate threaded portion 104 includes one or more apertures extending through a central, lengthwise axis of the nail 100. In the illustrated example, the elongate threaded portion 104 includes an aperture 112, an aperture 114, an aperture 116, and an aperture 118. In other examples, the elongate threaded portion 104 may include one, two, three, or another suitable quantity of apertures 112-118. As will be described more below, the one or more apertures 112-118 are sized and shaped to receive crossing screws as part of installing the nail 100. In some aspects, a central axis of an aperture 112-118 may be perpendicular to the central axis of the nail 100. In other aspects, a central axis of an aperture 112-118 may be non-perpendicular to the central axis of the nail 100.

In aspects in which the nail 100 has more than one aperture 112-118, in some examples, a central axis of one aperture (e.g., the aperture 112) may be at an angle to (e.g., nonparallel with) a central axis of another aperture (e.g., the aperture 114), which enables the installation of diverging crossing screws. For example, an angle between central axes of two apertures may be within the range of 10° to 40°. Diverging crossing screws can provide greater pullout strength, and therefore greater holding power, than parallel crossing screws. Nonetheless, in other examples, a central axis of one aperture may be parallel with a central axis of another aperture. For instance, a central axis of the aperture 112 may be parallel with the central axis of the aperture 114, or the central axis of the aperture 112 may be parallel with the central axis of the aperture 116 or 118.

The nail 100 may be constructed of a suitable biocompatible material. For example, stainless steel, a cobalt-chromium alloy, titanium, a titanium alloy, magnesium, or polyether ether ketone (PEEK) are suitable biocompatible materials.

FIGS. 2 and 3 illustrate an example of the nail 100 installed within an ulna 200 having a fractured olecranon, with FIG. 3 being a magnified view of a proximal end of the ulna 200 including the fractured olecranon. As shown, the ulna 200 includes a fracture 202 in the olecranon separating the ulna 200 into a first bone part 220 and a second bone part 222. The first bone part 220 is a fragment of the olecranon. The second bone part 220 includes the remaining portion of the ulna 200 (e.g., an olecranon fragment and distal ulna).

In the illustrated example, the nail 100 is shown installed with four crossing screws 204-210. The crossing screw 204 is positioned through the aperture 112, the crossing screw 206 through the aperture 114, the crossing screw 208 through the aperture 116, and the crossing screw 210 through the aperture 118. The crossing screw 204 and the crossing screw 206 are diverging crossing screws that are installed in the first bone part 222 at an angle to one another. Likewise, the crossing screw 208 and the crossing screw 210 are diverging crossing screws that are installed in the second bone part 220 at an angle to one another. As such, in this example, a set of diverging crossing screws are installed on either side of the fracture 202. In other examples, only the diverging crossing screws 204 and 206, or only the diverging crossing screws 208 and 210, may be installed. In other examples still, only one, two, or three of the crossing screws 204-210 may be installed or crossing screws in addition to the crossing screws 204-210 may be installed.

Figure 4A:
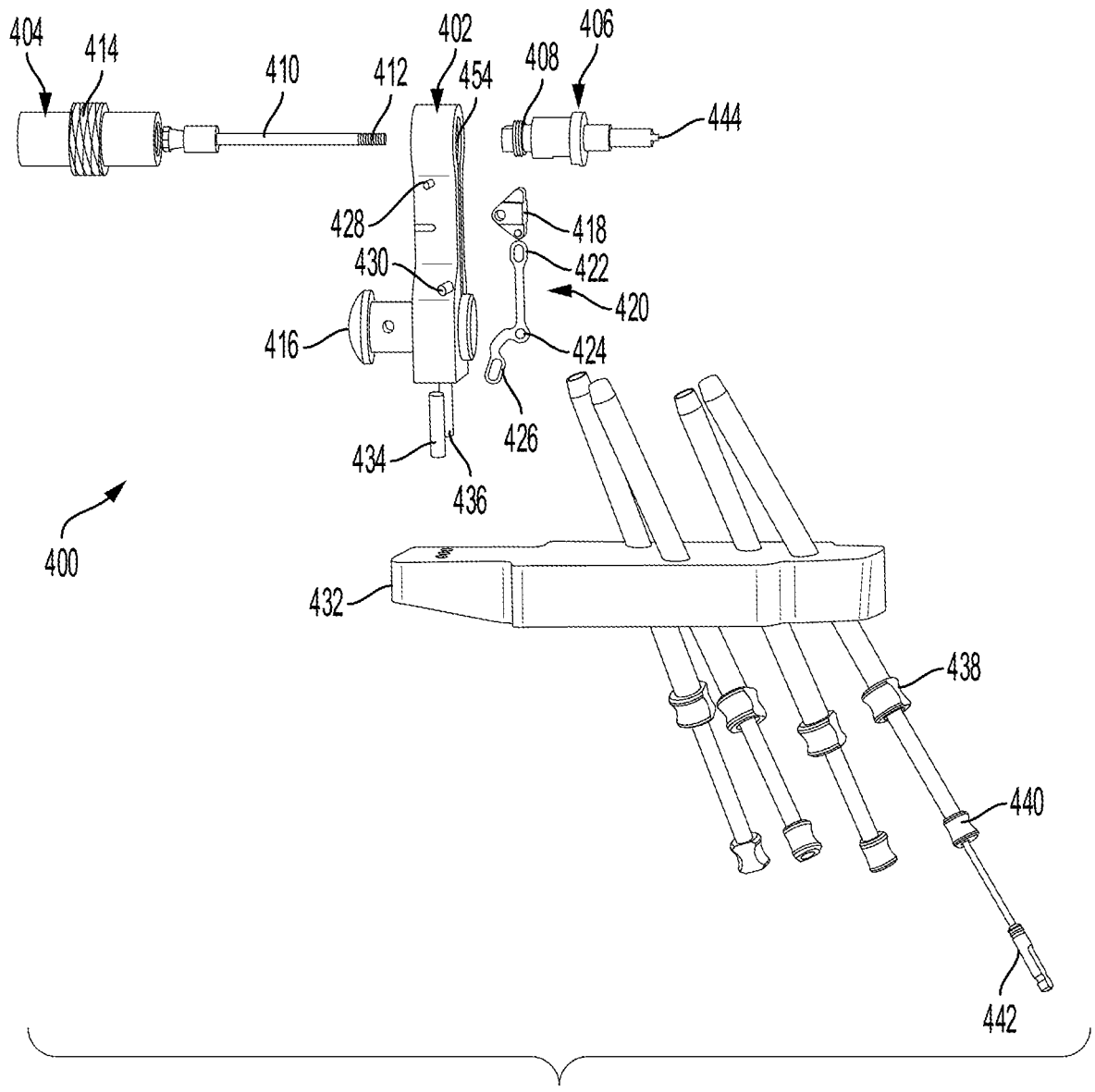
FIG. 4A illustrates an exploded view of a nail installation instrument, according to an aspect of the present disclosure.

FIG. 4A illustrates an exploded view of an example nail installation instrument 400 that may be used to install a nail (e.g., the nail 100). The example nail installation instrument 400 may include a first portion and a second portion that can rotate relative to one another. The first portion of the nail installation instrument 400 may be constructed to couple to the nail 100 and may be used to drive the nail 100 into bone during installation of the nail 100. In various aspects, the first portion of the nail installation instrument 400 may include an example connector 404. The connector 404 may include a nut having a gripping portion 414. The gripping portion 414 may help a surgeon manually turn the connector 404 when installing the nail 100. In some aspects, a trailing end of the nut of the connector 404 may have an interface for coupling to a driver (e.g., hand-driven or powered). In some aspects, a leading end of the nut of the connector 404 may have interior threading for coupling to an example bearing 406. The connector 404 may include a bolt 410. A leading end of the bolt 410 may have threading 412. A surgeon may engage the threading 412 with female threading at the trailing end 108 of the nail 100 to thereby couple the nail 100 to the connector 404.

Figure 4B:
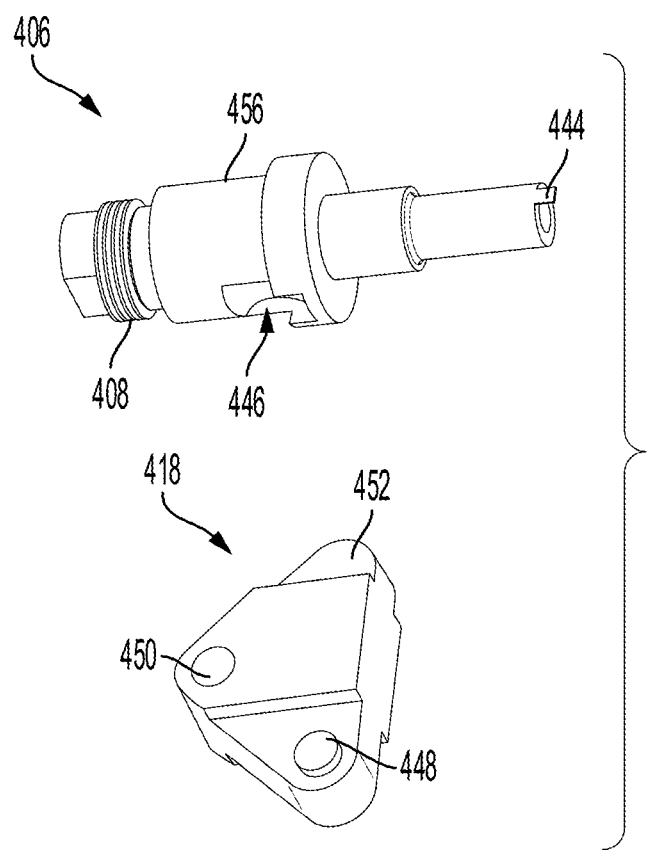
FIG. 4B illustrates perspective views of a bearing and a key of the nail installation instrument of FIG. 4A, according to an aspect of the present disclosure.

In various aspects, the first portion of the nail installation instrument 400 may include the example bearing 406, which is also illustrated in FIG. 4B and therefore reference is made to both FIGS. 4A and 4B when describing the bearing 406. The bearing 406 may include a hollow body 456. A channel extends through the hollow body 456 such that the bolt 410 may be positioned through the hollow body 456. A trailing end of the body 456 may include threading 408 for coupling to interior threading of the nut of the connector 404. A leading end of the body 456 may be constructed to engage with the trailing end 108 of the nail 100. For example, the leading end of the body 456 may include an extension 444 constructed to engage with the notch 300 of the trailing end 108 of the nail 100. Engagement of the bearing 406 with the nail 100 helps ensure a specific and consistent alignment of the nail 100 relative to the bearing 406. As described more below, the specific alignment of the nail 100 relative to the bearing 406 enables orienting the second portion of the nail installation instrument 400 so that it is aligned with the apertures 112-118 of the nail 100. Engagement of the bearing 406 with the nail 100 can also help increase insertion torque when installing the nail 100.

In various aspects, the hollow body 456 may include a lock interface in the form of a notch 446. In such aspects, the notch 446 is part of a locking mechanism for enabling or preventing rotation between the first and second portions of the nail installation instrument 400, which will be described more below. The notch 446, or other suitable lock interface, is positioned on the hollow body 456 relative to the extension 444 such that the apertures 112-118 of the nail 100 are in a specific orientation relative to the notch 446 when the nail 100 is engaged with the extension 444, as described more below.

The second portion of the nail installation instrument 400 is constructed, in part, as a guide for installing one or more crossing screws 204-210 through the one or more apertures 112-118 of the nail 100 when the nail 100 is within bone. In various aspects, the second portion of the nail installation instrument 400 includes a targeting block 432. The targeting block 432 may be coupled to the first portion of the nail installation instrument 400 via a targeting connector 402. For instance, the targeting connector 402 may include pins 434 and 436 for insertion into openings in the targeting block 432, thereby coupling the targeting block 432 to the targeting connector 402. In some examples, the pins 434 and 436 may be inserted into openings in a body of the targeting connector 402. In other examples, the pins 434 and 436 may be integral with the body of the targeting connector 402. In some aspects, the pins 434 and 436 may alternatively be integral with the targeting block 432. The targeting block 432 may be coupled to the targeting connector 402 via other suitable mechanisms, or may be integral with (e.g., non-removable from) the targeting connector 402, in other examples.

In various aspects, the targeting block 432 may include a plurality of guide holes. For illustrative purposes, cannulas 438 are shown positioned through the guide holes of the targeting block 432. The guide holes are oriented on the targeting block 432 such that a cannula 438 positioned through one of the guide holes aids in targeting a crossing screw (e.g., a crossing screw 204-210) through an aperture (e.g., an aperture 112-118) of the nail 100, as is known in the art. Smaller cannulas 440 are also illustrated as is a drill 442. In various instances, a smaller cannula 440 may be positioned within a cannula 438 to guide the drill 442. In such instances, the smaller cannula 440 may be removed and the cannula 438 may be used to guide a crossing screw for installation.

A body of the targeting connector 402 may include an opening 454 that enables coupling to the first portion of the nail installation instrument 400. For instance, the body 456 of the bearing 406 may be positioned through the opening 454. The bearing 406 may rotate freely within the opening 454 unless and until a locking mechanism of the targeting connector 402 is engaged. Stated differently, when the locking mechanism of the targeting connector 402 is disengaged, the first portion of the nail installation instrument 400 (e.g., the bearing 406) and the targeting connector 402 may rotate freely relative to one another, but when the locking mechanism of the targeting connector 402 is engaged, the first portion of the nail installation instrument 400 (e.g., the bearing 406) and the targeting connector 402 are fixed relative to one another.

The locking mechanism of the targeting connector 402 may have a variety of suitable constructions, a few non-limiting examples of which are described herein. In the example illustrated in FIG. 4A, the locking mechanism includes a key 418, which is also illustrated in FIG. 4B and therefore reference is made to both FIGS. 4A and 4B when describing the key 418. In various aspects, the key 418 may include a body having an end 452 sized to fit within the notch 446 of the bearing 406. The body of the key 418 may further include protrusions 448 (e.g., a protrusion 448 on either side of the body, though only one side is illustrated) and/or an opening 450. A pin 428 may be positioned through the opening 450 to couple the key 418 to the targeting connector 402.

The locking mechanism, in this example, further includes a lever 420. The lever 420 may include two split openings 422 such that the protrusion 448 on a first side of the body of the key 418 may be positioned within one opening 422 and the protrusion 448 on a second side of the body of the key 418 may be positioned within the other opening 422, thereby coupling the lever 420 to the key 418. A pin 430 may be positioned through an opening 424 of the lever 420 to thereby couple the lever 420 to the targeting connector 402. The lever 420 may further include an opening 426. In this example, the locking mechanism further includes a button 416. The button 416 may be coupled to the lever 420, such as by a pin through the opening 426 of the lever 420.

The locking mechanism of FIG. 4A operates as follows to enable or prevent relative rotation between the first and second portions of the nail installation instrument 400. With the button 416 at rest (e.g., undepressed), the end 452 of the key 418 is positioned within the notch 446 of the bearing 406. As such, the locking mechanism is engaged with the button 416 at rest and relative rotation is prevented between the first and second portions of the nail installation instrument 400. Stated differently, the bearing 406 and the targeting connector 402 may not rotate relative to one another with the button 416 at rest and the locking mechanism engaged.

When the button 416 is depressed, the lever 420 rotates about the pin 430 such that the openings 422 of the lever 420 translate towards the side of the targeting connector 402 including the button 416. The translation of the openings 422 causes the key 418 to rotate about the pin 428, thereby translating the end 452 of the key 418 out of the notch 446 of the bearing 406. As such, the locking mechanism is disengaged with the button 416 depressed and the first and second portions of the nail installation instrument 400 may rotate relative to one another. Stated differently, the bearing 406 and the targeting connector 402 may rotate relative to one another with the button 416 depressed and the locking mechanism disengaged.

The nail 100 and the nail installation instrument 400 are constructed such that, when the locking mechanism is engaged, the guide holes of the targeting block 432 (and therefore the cannulas 438, 440 when inserted) are aligned with the apertures 112-118 of the nail 100. The notch 300 may be specifically positioned on the trailing end 108 of the nail 100 relative to the apertures 112-118, and the extension 444 may be specifically positioned on the bearing 406 relative to the notch 446, such that the apertures 112-118 are in a specific orientation relative to the notch 446 when the extension 444 of the bearing 406 is engaged in the notch 300 of the nail 100. The specific orientation of the apertures 112-118 is an orientation such that the apertures 112-118 are aligned with the guide holes of the targeting block 432 when the key 418 is engaged in the notch 446. In this way, the locking mechanism may be disengaged to enable the first portion of the nail installation instrument 400 to rotate for insertion of the nail 100, and regardless of the orientation of the first portion (and thereby the nail 100) upon the nail 100 being inserted, the second portion of the nail installation instrument 400 may be rotated until the locking mechanism engages to align the guide holes of the targeting block 432 to the apertures 112-118 of the nail 100.

Figure 6:
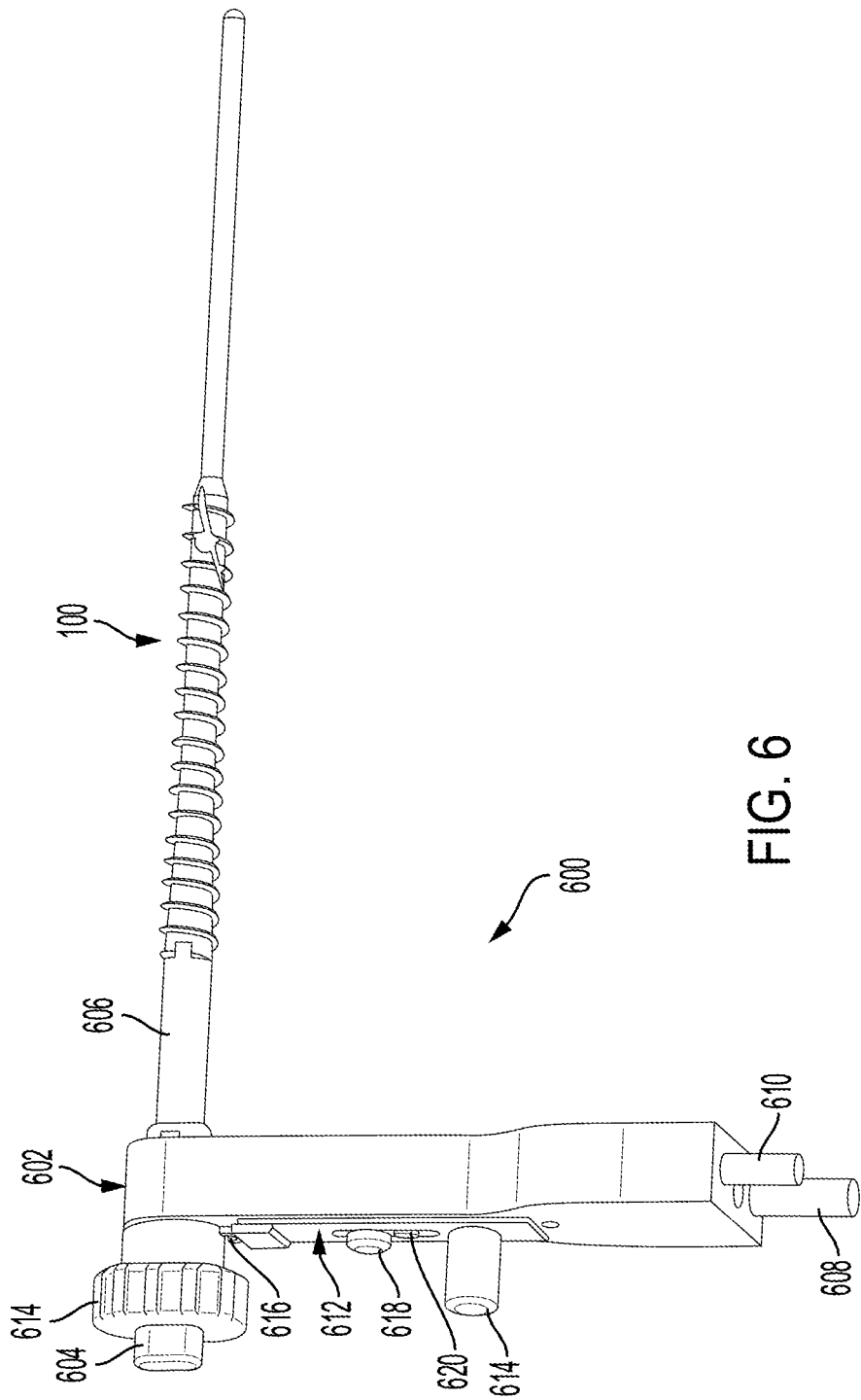
FIG. 6 illustrates a perspective view of a portion of an alternative nail installation instrument, according to an aspect of the present disclosure.

FIG. 6 illustrates a portion of an example nail installation instrument 600 having an alternative example locking mechanism. The example nail installation instrument 600 is shown coupled to a nail 100. In various aspects, the example nail installation instrument 600 may include a first portion that includes an example connector 604 and an example bearing 606. In this example, the bearing 606 includes a gripping portion 614. In various aspects, the example nail installation instrument 600 may include a second portion including a targeting connector 602. The second portion of the example nail installation instrument 600 may further include a targeting block (e.g., the targeting block 432) even though it is not illustrated. In this example, the targeting connector 602 includes integral pins 608 and 610 for coupling to a targeting block.

The targeting connector 602 of the nail installation instrument 600 includes an example sliding spring-based locking mechanism. The example sliding spring-based locking mechanism may include a lever 612. The lever 612 may include a key 616. The key 616 is shaped and sized to fit within a notch of the bearing 606. In various aspects, the lever 612 may include a handle 614. The lever 612 may be coupled to one end of a spring (not illustrated) that may be positioned within the targeting connector 602. The other end of the spring may be coupled to the targeting connector 602. Guide pins 618 and 620 ensure linear displacement of the lever 612 by being positioned within an opening of the lever 612 as illustrated. The guide pin 618 may include a button head that secures the lever 612 to the targeting connector 602.

The sliding spring-based locking mechanism of FIG. 6 operates as follows to enable or prevent relative rotation between the first and second portions of the nail installation instrument 600. With the lever 612 at rest, the spring maintains the key 616 of the lever 612 within the notch of the bearing 606. As such, the locking mechanism is engaged with the lever 612 at rest and relative rotation is prevented between the first and second portions of the nail installation instrument 600. Stated differently, the bearing 606 and the targeting connector 602 may not rotate relative to one another with the lever 612 at rest and the locking mechanism engaged.

The lever 612 may be translated away from the bearing 606 to disengage the locking mechanism. For example, a surgeon may pull the handle 614 to overcome the spring force and translate the lever 612 away from the bearing 606 such that the key 616 is removed from the notch of the bearing 606. As such, the locking mechanism is disengaged with the lever 612 translated away from the bearing 606 and the first and second portions of the nail installation instrument 600 may rotate relative to one another. Stated differently, the bearing 606 and the targeting connector 602 may rotate relative to one another with the lever 612 translated away from the bearing 606 and the locking mechanism disengaged.

Figure 7:
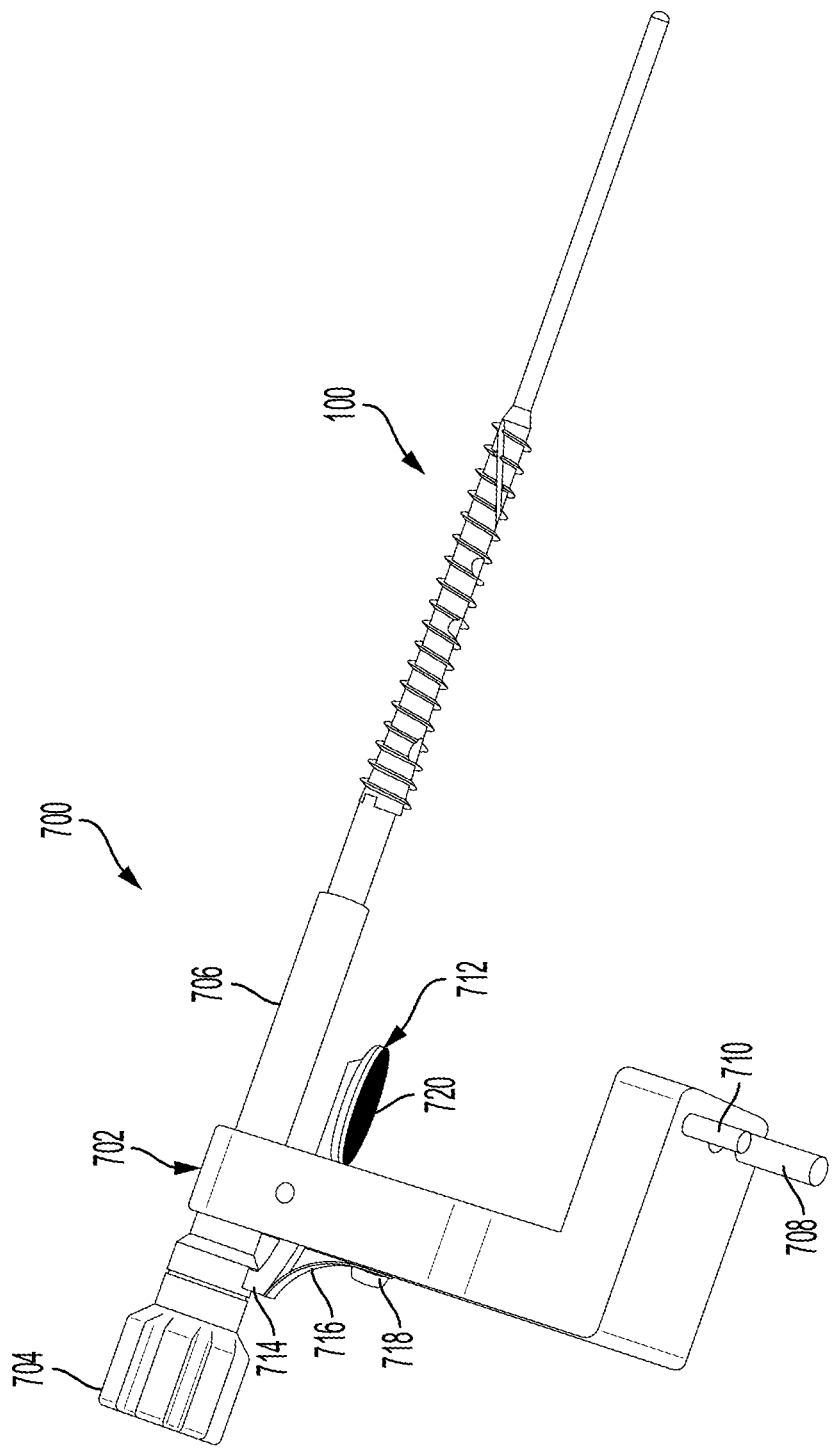
FIG. 7 illustrates a perspective view of a portion of an alternative nail installation instrument, according to an aspect of the present disclosure.

FIG. 7 illustrates a portion of an example nail installation instrument 700 having a further alternative example locking mechanism. The example nail installation instrument 700 is shown coupled to a nail 100. In various aspects, the example nail installation instrument 700 may include a first portion that includes an example connector 704 and an example bearing 706. In various aspects, the example nail installation instrument 700 may include a second portion including a targeting connector 702. The second portion of the example nail installation instrument 700 may further include a targeting block (e.g., the targeting block 432) even though it is not illustrated. In this example, the targeting connector 702 includes integral pins 708 and 710 for coupling to a targeting block.

The targeting connector 702 of the nail installation instrument 700 includes an example leaf spring-based locking mechanism. The example leaf spring-based locking mechanism may include a lever 712. The lever 712 may be coupled to the targeting connector 702 about a pivot axis. In various aspects, the lever 712 may be positioned through the targeting connector 702 as illustrated. The lever 712 may include a key 714. The key 714 is shaped and sized to fit within a notch of the bearing 706. The lever 712 is in contact with one end of a leaf spring 716. The opposite end of the leaf spring 716 may be fixedly attached to the targeting connector 702, such as with a screw 718.

The leaf spring-based locking mechanism of FIG. 7 operates as follows to enable or prevent relative rotation between the first and second portions of the nail installation instrument 700. With the lever 712 at rest, the leaf spring 716 maintains the key 714 of the lever 712 within the notch of the bearing 706. As such, the locking mechanism is engaged with the lever 712 at rest and relative rotation is prevented between the first and second portions of the nail installation instrument 700. Stated differently, the bearing 706 and the targeting connector 702 may not rotate relative to one another with the lever 712 at rest and the locking mechanism engaged.

The lever 712 may be rotated about its pivot axis to disengage the locking mechanism. For example, a surgeon may press the end 720 of the lever 712 to overcome the spring force of the leaf spring 716 and rotate the lever 712 such that the key 714 is removed from the notch of the bearing 706. As such, the locking mechanism is disengaged with the end 720 of the lever 712 depressed and the first and second portions of the nail installation instrument 700 may rotate relative to one another. Stated differently, the bearing 706 and the targeting connector 702 may rotate relative to one another with the end 720 of the lever 712 depressed and the locking mechanism disengaged.

Figure 5:
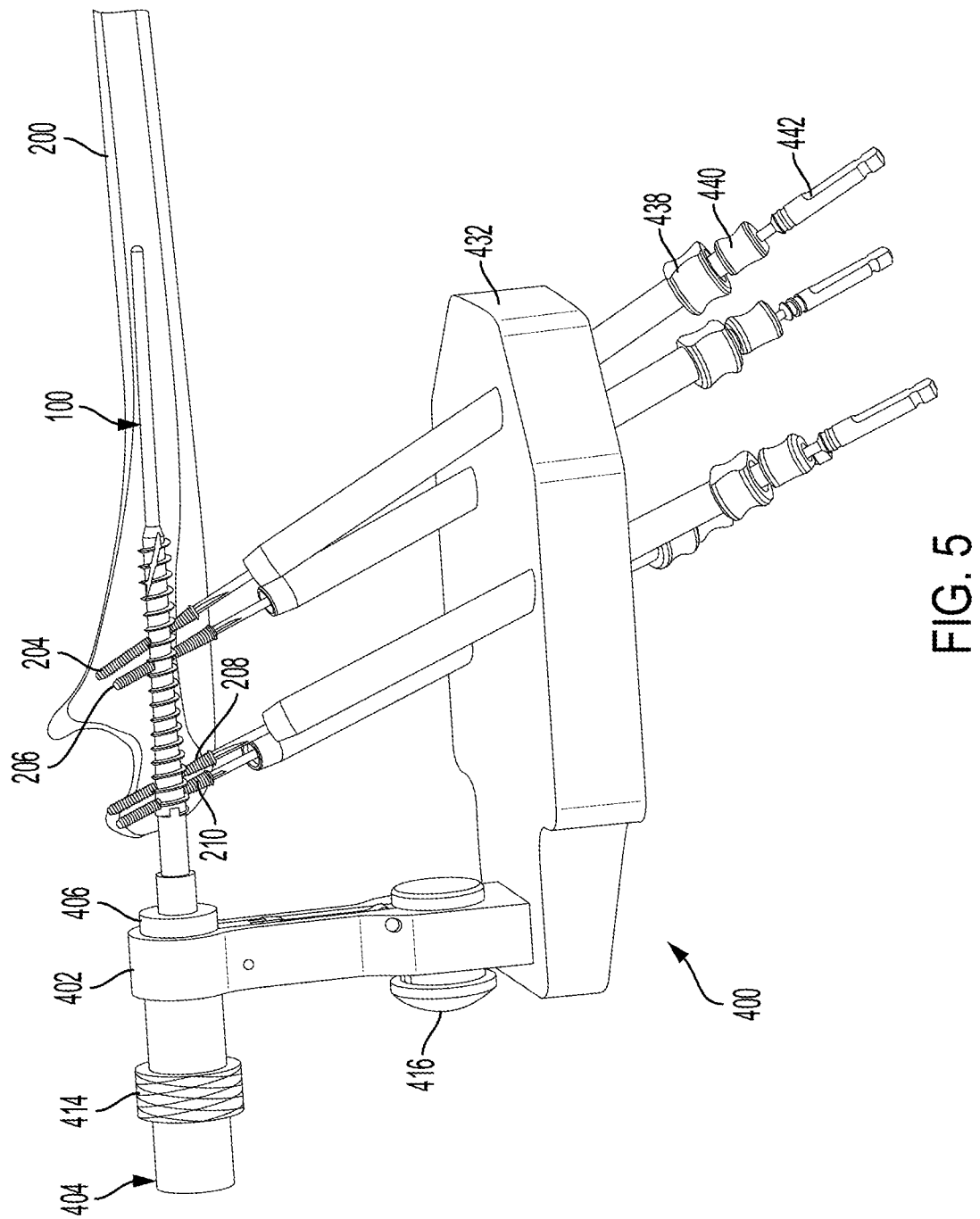
FIG. 5 illustrates the nail installation instrument of FIG. 4 coupled to a nail installed within an ulna, according to an aspect of the present disclosure.

FIG. 5 illustrates the example nail installation instrument 400 coupled to an example of a nail 100 installed within an ulna 200. Cannulas 438, 440 and drills 442 are shown solely for illustrative purposes. An example method for a surgeon to install a nail (e.g., the nail 100) as shown in FIG. 5 using the example nail installation instrument 400 will now be described. It will be appreciated that many other methods of performing the acts associated with the example method may be used. For example, the order of some of the actions may be changed, certain actions may be combined with other actions, some of the actions described are optional, and the actions may be performed in relation to a different bone.

A surgeon may first make an incision (e.g., at the elbow) to expose an entry site for the nail 100 in bone (e.g., the proximal ulna including the olecranon). The surgeon may then reduce a fracture or osteotomy between two bone parts of the olecranon. An entry hole for the nail 100 may be drilled into the exposed olecranon. In some aspects, the surgeon may insert the nail 100 part way into the pre-drilled hole prior to coupling the nail installation instrument 400 to the nail 100. In other aspects, such as this example, the surgeon couples the nail 100 to the nail installation instrument 400 and then inserts the nail 100 into the pre-drilled hole until the thread 110 of the elongate threaded portion 104 engages the olecranon. At this point, the surgeon may disengage the locking mechanism of the nail installation instrument 400. For example, the surgeon may depress the button 416. With the button 416 depressed and the locking mechanism disengaged, the surgeon may advance the nail 100 into the olecranon and distal ulna by rotating the connector 404 either directly or with a driver. The nail 100 may be advanced into the olecranon and distal ulna until the trailing end 108 of the nail 100 is flush with the cortex of the olecranon.

The surgeon may then release the button 416, though the locking mechanism is not yet engaged since the end 452 of the key 418 is not aligned with the notch 446 of the bearing 406, and therefore not positioned within the notch 446. The surgeon may then rotate the targeting connector 402 relative to the bearing 406 until the end 452 of the key 418 is positioned within the notch 446, thereby engaging the locking mechanism. It will be appreciated that this same rotation until the locking mechanism is engaged can be achieved with the locking mechanisms of the example nail installation instruments 600 and 700 described above. If it is not already attached, the surgeon may then couple the targeting block 432 to the targeting connector 402. Cannulas 438 and 440 may be inserted through the guide holes of the targeting block 432 and the surgeon may position a drill 442 through a cannula 440 to drill a hole into the olecranon and through an aperture 112, 114, 116, or 118 of the nail 100. This may be repeated for however many crossing screws 204-210 are to be installed through the nail 100. The cannulas 440 may then be removed and a crossing screw 204-210 may be guided through a cannula 438 and installed with a driver through an aperture 112, 114, 116, or 118 of the nail 100. This may be repeated for however many crossing screws 204-210 are to be installed through the nail 100. The nail installation instrument 400 may then be decoupled from the installed nail 100 and the soft tissue at the entry site may be closed.

In this way, the surgeon is able to rotate the connector 404 and the bearing 406 relative to the targeting connector 402 in order to advance the nail 100 into the ulna, rotate the targeting connector 402 relative to the connector 404 and the bearing 406 in order to properly align the targeting block 432 for crossing screw installation, and then lock these components relative to one another in order to install the crossing screws. This installation method would not be possible with a typical nail installation instrument that is incapable of such relative rotation.

In the present disclosure, the terms "including" and "comprising" are used in an open-ended fashion, and thus should be interpreted to mean "including, but not limited to . . . " As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

Reference throughout the specification to "various aspects," "some aspects," "some examples," "other examples," or "one aspect" means that a particular feature, structure, or characteristic described in connection with the aspect is included in at least one example. Thus, appearances of the phrases "in various aspects," "in some aspects," "certain embodiments," "some examples," "other examples," "certain other embodiments," or "in one aspect" in places throughout the specification are not necessarily all referring to the same aspect. Furthermore, the particular features, structures, or characteristics illustrated or described in connection with one example may be combined, in whole or in part, with features, structures, or characteristics of one or more other aspects without limitation.

It is to be understood that at least some of the figures and descriptions herein have been simplified to illustrate elements that are relevant for a clear understanding of the disclosure while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements may not be provided herein.

The terminology used herein is intended to describe particular embodiments only and is not intended to be limiting of the present disclosure. As used herein, the singular forms "a," "an," and "the" are intended to include the plural forms as well, unless otherwise indicated. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term 'at least one of X or Y' or 'at least one of X and Y' should be interpreted as X, or Y, or X and Y.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, any suitable combination of features of the various examples described is contemplated.

The invention is claimed as follows:

1. A system for compressing a first bone part and a second bone part separated by a fracture, the system comprising:
   a nail having an elongate smooth portion and an elongate threaded portion, the elongate smooth portion including a leading end of the nail and the elongate threaded portion including a trailing end of the nail, the elongate threaded portion including a first end opposite the trailing end and a thread extending from the first end to the trailing end, wherein the thread has a decreasing pitch from the first end to the trailing end, and wherein the elongate threaded portion further includes at least one aperture extending through a central axis of the nail, a central axis of one of the at least one aperture is non-perpendicular to the central axis of the nail; and
   at least one screw sized to be positioned through the at least one aperture;
   a nail installation instrument comprising:
      a first portion configured to couple to the trailing end of the nail;
      a second portion having a targeting connector coupled to a targeting block and to the first portion of the nail installation instrument, the targeting block including a plurality of guide holes; and
      a plurality of cannulas configured to be inserted into the guide holes of the targeting block,
      wherein the first portion of the nail installation instrument is configured to rotate with the coupled nail independently from the second portion of the nail installation instrument,
   wherein the at least one aperture comprises a first aperture and a third aperture each extending through the central axis of the nail,
   wherein the first and third apertures are positioned along the elongate threaded portion such that, when the elongate threaded portion of the nail is installed across the fracture separating the first bone part and the second bone part, the first aperture is within the first bone part and the third aperture is within the second bone part.

2. The system of claim 1, wherein the at least one aperture further comprises a second aperture extending through the central axis of the nail.

3. The system of claim 2, wherein a central axis of the first aperture is at an angle to a central axis of the second aperture.

4. The system of claim 2, wherein the at least one aperture further comprises a fourth aperture extending through the central axis of the nail.

5. The system of claim 4, wherein a central axis of the third aperture is at an angle to a central axis of the fourth aperture.

6. The system of claim 4, wherein the second and fourth apertures are positioned along the elongate threaded portion such that, when the elongate threaded portion of the nail is installed across the fracture separating the first bone part and the second bone part, the second aperture is within the first bone part and the fourth aperture is within the second bone part.

7. The system of claim 1, wherein the targeting connector is configured to translate a key into or out of a slot of the first portion of the nail installation instrument so as to respectively prevent or enable rotation of the first portion of the nail installation instrument relative to the second portion of the nail installation instrument.

8. The system of claim 1, wherein the first bone part is a first olecranon fragment and the second bone part includes a distal ulna.

9. A method for compressing a first bone part and a second bone part separated by a fracture, the method comprising:
   forming a hole in the first bone part, across the fracture, and in the second bone part;
   coupling a nail installation instrument to a nail, the nail having an aperture extending through a central axis of the nail;
   inserting part of the nail into the formed hole;
   rotating a first portion of the nail installation instrument independent of a second portion of the nail installation instrument thereby installing the nail in the formed hole;
   rotating the second portion of the nail installation instrument independent of the first portion of the nail installation instrument thereby aligning the second portion of the nail installation instrument with respect to the aperture of the installed nail; and
   installing a screw into the first bone part or the second bone part and through the aperture of the installed nail.

10. The method of claim 9, wherein the nail installation instrument is coupled to the nail prior to inserting part of the nail into the formed hole.

11. The method of claim 9, further comprising locking the second portion of the nail installation instrument relative to the first portion of the nail installation instrument upon the second portion of the nail installation instrument being aligned with respect to the aperture of the installed nail.

12. The method of claim 9, wherein the second portion of the nail installation instrument includes a targeting block having a plurality of guide holes, the method further comprising inserting a cannula through a guide hole of the targeting block such that the cannula is aligned with the aperture of the installed nail.

13. The method of claim 12, wherein the hole is a first hole, the method further comprising inserting a drill through the cannula and forming, via the drill, a second hole in the first bone part or the second bone part and through the aperture of the installed nail.

14. The method of claim 9, wherein the nail has an elongate smooth portion and an elongate threaded portion, the elongate smooth portion including a leading end of the nail and the elongate threaded portion including a trailing end of the nail, the elongate threaded portion including a first end opposite the trailing end and a thread extending from the first end to the trailing end, wherein the thread has a decreasing pitch from the first end to the trailing end.

15. The method of claim 14, wherein the nail is installed in the formed hole such that the elongate threaded portion is positioned in both the first bone part and the second bone part and across the fracture.

16. The method of claim 15, wherein installing the nail in the formed hole thereby compresses the first bone part and the second bone part against one another at the fracture.

17. The method of claim 14, wherein the part of the nail that is inserted into the formed hole is the elongate smooth portion of the nail, wherein the elongate smooth portion of the nail is inserted into the formed hole prior to rotating the first portion of the nail installation instrument independent of the second portion of the nail installation instrument.

18. The method of claim 9, wherein the first bone part is a first olecranon fragment and the second bone part includes a distal ulna.

* * * * *